United States Patent [19]
Higley et al.

[11] Patent Number: 5,478,830
[45] Date of Patent: Dec. 26, 1995

[54] FUSED-RING HETEROCYCLES FOR THE TREATMENT OF ATHEROSCLEROSIS

[75] Inventors: C. Anne Higley, Newark; Ruth R. Wexler, Wilmington; Richard G. Wilde, New Castle, all of Del.

[73] Assignee: The Du Pont Merck Pharmaceutical Company, Wilmington, Del.

[21] Appl. No.: 889,892

[22] Filed: May 29, 1992

[51] Int. Cl.⁶ .................... C07D 487/04; A61K 31/505; A61K 31/52; A61K 31/44

[52] U.S. Cl. .................... 514/258; 544/262; 544/264; 544/276; 544/277; 544/271; 544/272; 546/118; 546/119

[58] Field of Search .................... 514/258; 544/262

[56] References Cited

PUBLICATIONS

Noell, JO$_{vg}$ Chem 23, 1547 (1958).

Primary Examiner—Mark L. Berch

[57] ABSTRACT

This invention relates to pyrazolo pyrimidines for the treatment of atherosclerosis as inhibitors of acyl—CoA, cholesterol acyetransferase (ACAT), and their use as antihypercholesterolemic agents, pharmaceutical compositions and preparation, and having the formula (I):

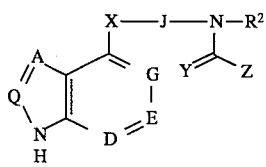

wherein:

A and Q are selected independently from CH or N with no more than two nitrogens per ring:

D, E, and G are selected independently from $CR^1$ or N with no more than two nitrogens per ring;

X is $S(O)_r$, O, $NR^4$ or $CH^2$;

J is $C_2$–$C_{10}$ alkyl, $C_3$–$C_{10}$ branched alkyl, $C_3$–$C_{10}$ alkenyl or $C_3$–$C_{10}$ alkynyl;

Y is O, S, $H_2$ or NH:

Z is $NHR^3$, $OR^3$ or $R^3$:

$R^1$ is selected independently from H, $NO_2$, Br, Cl, F, $CF_3$, CN, $CH_3S(O)_r$, $C_1$–$C_8$ alkyl or alloxy, $C_3$–$C_8$ branched alkyl, $C_1$–$C_4$ carboalkoxy, $NR^5R^6$ or $NR^5COR^6$;

$R^2$ is $C_1$–$C_8$ alkyl, $C_3$–$C_8$ branched alkyl, $C_3$–$C_7$ cycloalkyl, $C_3$–$C_8$ alkenyl or alkynyl, $C_7$–$C_{14}$ araalkyl where the aryl group is optionally substituted; phenyl optionally substituted benzyl optionally substituted 2-, 3-, or 4- pyridinyl, pyrimidinyl: or biphenyl:

$R^3$ is $C_1$–$C_8$ alkyl, $C_3$–$C_8$ branched alkyl, $C_3$–$C_7$ cycloalkyl, $C_4$–$C_{10}$ cycloallylalkyl, $C_3$–$C_6$ alkenyl or alkynyl, $C_1$–$C_3$ perfluoroalkyl, $C_7$–$C_{14}$ araalkyl where the aryl group is optionally substituted phenyl optionally substituted benzyl optionally substituted 2-, 3-, or 4- pyridinyl, pyrimidinyl; or biphenyl:

$R^4$ is H, $C_1$–$C_6$ alkyl or benzyl;

$R^5$ and $R^6$ are selected independently from H or $C_1$–$C_4$ alkyl;

r is 0 to 2:

or a pharmaceutically acceptable salt thereof.

12 Claims, No Drawings

FUSED-RING HETEROCYCLES FOR THE TREATMENT OF ATHEROSCLEROSIS

FIELD OF THE INVENTION

This invention relates to imidazoles as inhibitors of acyl-CoA: cholesterol acyltransferase (ACAT), pharmaceutical compositions containing them, processes for their preparation, and their use as antihypercholesterolemic and/or anti-atherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There is an increasing number of patents in the literature disclosing compounds which are useful as ACAT inhibitors in particular and antiatherosclerotic agents in general. For example, U.S. Pat. No. No. 4,623,662, issued to De Vries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol.

U.S. Pat. No. 4,868,210, issued to Trivedi on Sep. 19, 1989, as well as U.S. Pat. No. 4,923,896, May 8, 1990, disclose certain N-2,6-dialkyl- or N- 2,6-dialkoxyphenyl-N'-arylalkyl ureas as potent inhibitors of ACAT.

European Patent Application 354,994, filed by Meguro and Ikeda which published on Feb. 21,1990, discloses certain N-aryl-N'-quinolin-4-yl ureas as ACAT inhibitors. European Patent Application 370,740, filed by Jackson et al. which published on May 30, 1990, discloses ACAT inhibitors similar in composition to those of deVries (vide supra) but different in constitution.

Billheimer, et al., European Patent Application EP-A-372,445, published on Jun. 13, 1990, discloses compounds of the formula:

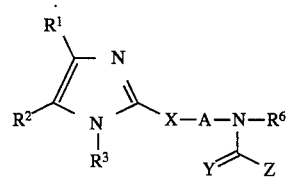

wherein $R^1$ and $R^2$ are selected independently from H, $C_1$–$C_8$ alkyl, $C_3$–$C_8$ branched alkyl, $C_3$–$C_7$ cycloalkyl, $C_4$–$C_{10}$ cycloalkylalkyl, $C_7$–$C_{14}$ araalkyl, 2-, 3- or 4pyridinyl, 2-thienyl, 2-furanyl, phenyl optionally substituted with 1 to 3 groups selected from F, Cl, Br, OH, $C_1$–$C_4$ alkoxy, $C_1$–$C_4$ alkyl, $C_3$–$C_8$ branched alkyl, $CH_3S(O)_r$, $NO_2$, $CF_3$, or $NR^7R^8$; or $R^1$ and $R^2$ can also be taken together as

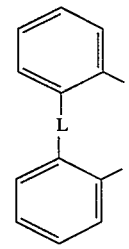

where L is O, $O(CH_2)_{m+1}O$, or $(CH_2)_m$ where m is 0–4;

$R^3$ is H, $C_1$–$C_6$ alkyl, allyl, benzyl, or phenyl optionally substituted with F, Cl, $CH_3$, $CH_3O$, or $CF_3$;

$R^4$ is straight chain $C_1$–$C_8$ alkyl optionally substituted with F; $C_3$–$C_8$ branched alkyl, $C_3$–$C_7$ cycloalkyl, $C_4C_{10}$ cycloalkylalkyl, $C_7$–$C_{14}$ araalkyl where the aryl group is optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$, or $NCOR^7$; $C_3$–$C_6$ alkenyl or alkynyl, $C_1$–$C_3$ perfluoroalkyl, phenyl optionally substituted with 1 to 3 groups selected from $C_1$–$C_4$ alkyl, $C_3$–$C_8$ branched alkyl, $C_1$–$C_4$ alkoxy, F, Br, Cl, $NH_2$, OH, CN, $CO_2H$, $CF_3$, $NO_2$, $C_1$–$C_4$ carboalkoxy, $NR^7R^8$ or $NCOR^7$; pentafluorophenyl, benzyl optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$ or $NCOR^7$; 2-, 3- or 4- pyridinyl, pyrimidinyl, or biphenyl;

$R^5$ is H, $C_1$–$C_6$ alkyl, or benzyl;

$R^6$ is $C_1$–$C_8$ alkyl, $C_3$–$C_8$ branched alkyl, $C_3$–$C_7$ cycloalkyl, $C_3$–$C_8$ alkenyl or alkynyl, phenyl optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$, or $NCOR^7$; pentafluorophenyl, benzyl optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$, or $NCOR^7$;

$R^7$ and $R^8$ are selected independently from H or $C_1$–$C_4$ alkyl;

X is $S(O)_r$, O, $NR^5$, $CH_2$;

A is $C_2$–$C_{10}$ alkyl, $C_3$–$C_{10}$ branched alkyl, $C_3$–$C_{10}$ alkenyl, or $C_3$–$C_{10}$ alkynyl;

Y is O, S, H$_2$, NH;

Z is NHR$^4$, OR$^4$, or R$^4$;

r is 0–2, or a pharmaceutically acceptable salt thereof.

These compounds are potent in vitro inhibitors of ACAT and are therefore potential antihypercholesterolemic agents.

U.S. Pat. No. 4,900,744, issued to Billheimer et al. on Feb. 13, 1990, discloses antihypercholesterolemic thioimidazoles of the formula:

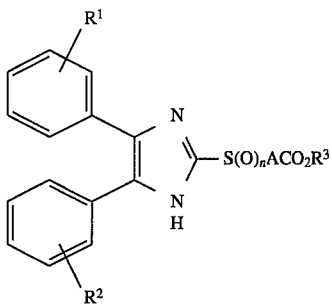

or a pharmaceutically acceptable salt thereof, wherein

R$^1$ and R$^2$ independently are H, F, Cl, CF$_3$, alkyl of 1 to 4 carbon atoms, or alkoxy of 1 to 4 carbon atoms;

A is alkylene of 7–20 carbon atoms of an alkenyl residue thereof with no more than 2 double bonds;

R$^3$ is H, CH$_3$, of C$_2$H$_5$; and n is 0, 1 or 2, such as 8-(4,5-diphenyl-1H-imidazol-2-ylthio)octanoic acid ethyl ester.

U.S. Pat. No, 4,460,598, issued to Lautenschläger et al. on Jul. 17, 1984, discloses compounds of the formula:

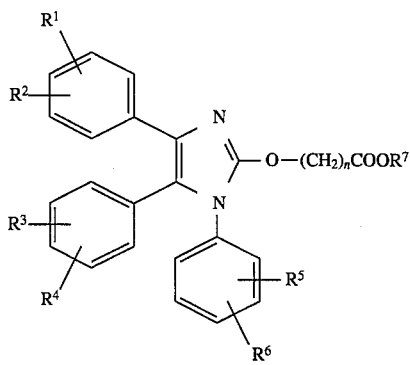

wherein

R$^1$, R$^2$, R$^3$, R$^4$, R$^5$ and R$^6$ independently are H, F, Cl, Br, I, alkyl, alkoxy, or CF$^3$, with the proviso that one or several of R$^1$ and R$^2$, R$^3$ and R$^4$ or R$^5$ and R$^6$ taken together represent methylenedioxy;

R$^7$ is H, alkali metal ion, alkyl of 1 to 6 carbon atoms, or benzyl; and n is 0 to 10.

The synthesis and the use of these compounds in the treatment of thromboembolic, inflammatory and/or atherosclerotic diseases is disclosed.

U.S. Pat. No. 4,654,358, issued to Lautenschläger et al. on Mar. 31, 1987, discloses compounds of the formula:

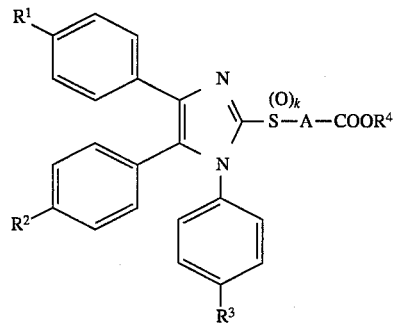

wherein k is 0, 1, or 2,

R$^1$, R$^2$ and R$^3$ independently are H, F, Cl, CH$_3$, CH$_3$O, or CF$_3$;

R$^4$ is H, Na, K, CH$_3$, CH$_3$CH$_2$, (CH$_3$)$_2$CH, CH$_3$(CH$_2$)$_2$, or butyl;

A is C(CH$_3$)$_2$, CH(CH$_2$)$_m$CH$_3$, (CH$_2$)$_n$, or (CH$_2$)$_{n-2}$CH(CH$_3$);

m is 0 to 8; and n is 2 to 10.

The synthesis and the use of these compounds in the treatment of inflammatory diseases, diseases of lipid metabolism, and/or hyperlipidemic diseases is disclosed.

German Laid Open Application No. DE 3504679, Lautenschläger et al., published Aug. 14, 1986, discloses compounds of the formula:

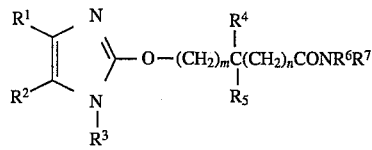

wherein

R$^1$, R$^2$ and R$^3$ independently are H, alkyl of 1 to 6 carbon atoms, cycloalkyl of 1 to 6 carbon atoms, or

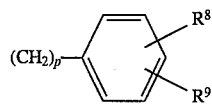

R$^4$ and R$^5$ independently are H, C$_6$H$_5$, or alkyl of 1 to 9 carbon atoms;

R$^6$ and R$^7$ independently are H, OH, saturated or unsaturated alkyl, cycloalkyl, or hydroxyalkyl of 1 to 10 carbon atoms,

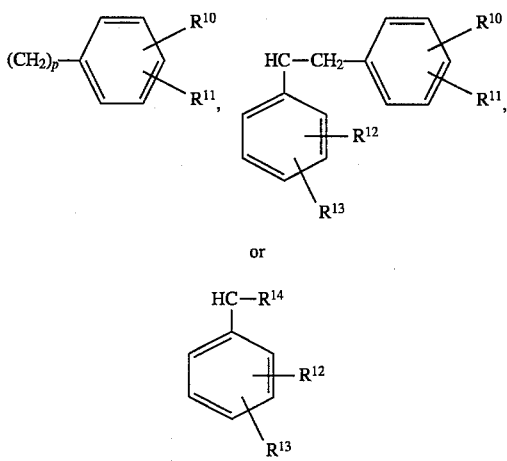

or

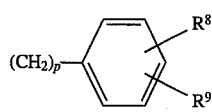

$R^8$, $R^9$, $R^{10}$, $R^{11}$, $R^{12}$ and $R^{13}$ independently are H, F, Cl, BE, $NO_2$, $CH_3CONH$, OR, alkyl of 1 to 3 carbon atoms, $CF_3$, and alkoxy of 1 to 3 carbon atoms, with the proviso that $R^8$ and $R^9$, $R^{10}$ and $R^{11}$, or $R^{12}$ and $R^{13}$ taken together represent methylenedioxy;

$R^{14}$ is alkyl of 1 to 2 carbon atoms;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

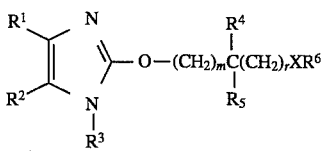

wherein $R^1$, $R^2$ and $R^3$ independently are H, alkyl of 1 to 6 carbon atoms, cycloalkyl of 1 to 6 carbon atoms, or

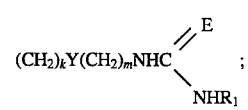

$R^1$ and $R^2$ can be taken together with the carbon atoms in the 4 and 5 position of the imidazole ring to represent a carbocyclic five- or six-membered aromatic or partially hydrogenated ring which may be substituted by $R^8$ or $R^9$;

$R^4$ and $R^5$ independently are H, $C_6H_5$, or alkyl of 1 to 9 carbon atoms;

$R^6$ is alkyl, cycloalkyl, or hydroxyalkyl of 1 to 20 carbon atoms, H, alkali metal if X is —COO—, 1-phenethyl, or

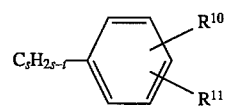

$R^7$ is H, OH if X is —$CONR^7$— or alkyl of 1 to 4 carbon atoms;

$R^8$, $R^9$, $R^{10}$ and $R^{11}$ are independently H, Cl, F, Br, $NO_2$, $CH_3CONH$, OH, alkyl of 1 to 3 carbon atoms, $CF_3$, or alkoxy of 1 to 3 carbons, or $R^8$ and $R^9$ or $R^{10}$ and $R^{11}$ taken together represent methylenedioxy;

X is a bond, O, OC (=O)O, C(=O) O, $CONR^7$ OC (=O), or OC(=O) $NR^7$;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

Durant et al., U.S. Pat. No. 4,228,291, issued Oct. 14, 1980, teaches compounds of the formula:

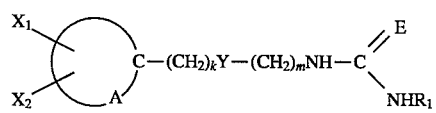

wherein

A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole, or 5, 6, 7,8-tetrahydroimidazol[ 1, 5-a] pyridine ring;

$X_1$ is H, lower alkyl, hydroxyl, trifluoromethyl, benzyl, halogen, amino, or $$(CH_2)_k Y(CH_2)_m NHC \overset{\displaystyle E}{\underset{\displaystyle NHR_1}{\diagdown}} ;$$

$X_2$ is H, or when $X_1$ is lower alkyl, lower alkyl or halogen;

k is 0 to 2;

m is 2 or 3, provided that the sum of k and m is 3 or 4;

Y is O, S, or NH;

E i s $NR_2$;

$R_1$ is H, lower alkyl or di-lower alkyl amino-lower alkyl; and $R_2$ is H, nitro, or cyano.

The compounds are said to be antihistamines of the $H_2$ receptor blocking type, as well as having anti-inflammatory activity.

White, U.S. Pat. No. 4,413,130, Nov. 1, 1983, discloses histamine $H_2$ receptor antagonists of the formula:

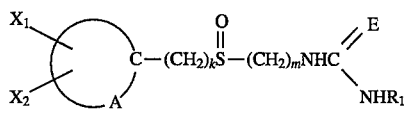

wherein

A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine;

$X_1$ and $X_2$ may be H, lower alkyl, trifluoromethyl, hydroxyl, halogen, amino, or $X_1$ and $X_2$ and at least two of the atoms comprising A may form a further ring;

k is 0 to 2;

m is 2 or 3, provided that the sum of k and m is 3 or 4;

E is O, S, or $NR_2$;

$R_1$ is H, lower alkyl, acyl, or dialkylaminoalkyl; and $R_2$ is H, $NO_2$, CN, alkanesulfonyl or arenesulfonyl.

There are no known literature references disclosing the compounds of this invention, their use as ACAT inhibitors, or their use to lower cholesterol or in the treatment of atherosclerosis.

The compounds of this invention are very potent ACAT inhibitors and thus are expected to be useful in pharmaceutical formulations for the treatment of atherosclerosis. This invention should not be construed as limited to any particular antihypercholesterolemic mechanism of action.

SUMMARY OF THE INVENTION

The present invention provides novel compounds of Formula (I), processes for their preparation, pharmaceutical compositions cantaining such fused-ring heterocycles, and therapeutic methods for their use as antihypercholesterolemic agents.

This invention provides compounds of Formula (I):

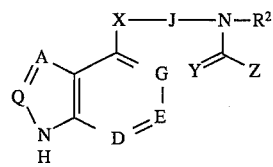

wherein:

A and Q are selected independently from CH or N with no more than two nitrogens per ring;

D, E, and G are selected independently from $CR^1$ or N with no more than two nitrogens per ring;

X is $S(O)_r$, O, $NR^4$ or $CH_2$;

J is $C_2$–$C_{10}$ alkyl, $C_3$–$C_{10}$ branched alkyl, $C_3$–$C_{10}$ alkenyl or $C_3$–$C_{10}$ alkynyl;

Y is O, S, $H_2$ or NH;

Z is $NHR^3$ $OR^3$ or $R^3$;

$R^1$ is selected independently from H, Br, Cl, F, $CF_3$, CN, $NO_2$, $CH_3S(O)_r$, $C_1$–$C_8$ alkyl or alkoxy, $C_3$–$C_8$ branched alkyl, $C_1$–$C_4$ carboalkoxy, $NR^5R^6$ or $NR^5COR^6$;

$R^2$ is $C_1$–$C_8$ alkyl, $C_3$–$C_8$ branched alkyl, $C_3$–$C_7$ cycloalkyl, $C_3$–$C_8$ alkenyl or alkynyl, $C_7$–$C_{14}$ araalkyl where the aryl group is optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; phenyl optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$ or $NR^5COR^6$; benzyl optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; 2-, 3-, or 4- pyridinyl, pyrimidinyl; or biphenyl;

$R^3$ is $C_1$–$C_8$ alkyl, $C_3$–$C_8$ branched alkyl, $C_3$–$C_7$ cycloalkyl, $C_4$–$C_{10}$ cycloalkylalkyl, $C_3$–$C_6$ alkenyl or alkynyl, $C_1$–$C_3$ perfluoroalkyl, $C_7$–$C_{14}$ araalkyl where the aryl group is optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; phenyl optionally substituted with 1 to 3 groups selected from $C_1$–$C_4$ alkyl or alkoxy, $C_3$–$C_8$ branched alkyl, F, Br, Cl, OH, CN, $CO_2H$, $CF_3$, $C_1$–$C_4$ carboalkoxy, $NR^5R^6$ or $NR^5COR^6$; benzyl optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$ or $NR^5COR^6$; 2-, 3-, or 4-pyridinyl, pyrimidinyl; or biphenyl;

$R^4$ is H, $C_1$–$C_6$ alkyl or benzyl;

$R^5$ and $R^6$ are selected independently from H or $C_1$–$C_4$ alkyl;

r is 0 to 2;

or a pharmaceutically acceptable salt thereof.

More preferred are compounds of Formula (I) wherein:

X is $S(O)_r$;

J is $C_2$–$C_{10}$ alkyl or $C_4$–$C_9$ branched alkyl;

Y is O;

Z is $NHR^3$;

$R^1$ is selected independently from H, $NO_2$, $C_1$–$C_8$ alkyl or alkoxy, $C_3$–$C_8$ branched alkyl, $C_1$–$C_4$ carboalkoxy, $NR^5R^6$ or $NR^5COR^6$;

$R^2$ is $C_1$–$C_8$ alkyl, $C_3$–$C_8$ branched alkyl, $C_3$–$C_7$ cycloalkyl, $C_7$–$C_{14}$ araalkyl where the aryl group is optionally substituted with 1 to 3 groups selected from $CH_3$, $CH_3O$, F, Br, Cl, OH, CN, $CO_2H$, $CF_3$, $NH_2$, $NO_2$, or di($C_1$–$C_4$) alkylamino; phenyl optionally substituted with 1 to 3 groups selected from $CH_3$, $CH_3O$, F, Br, Cl, OH, CN, $CO_2H$, $CF_3$, $NH_2$, $NO_2$, or di($C_1$–$C_4$) alkylamino; benzyl optionally substituted with 1 to 3 groups selected from $CH_3$, $CH_3O$, F, Br, Cl, OH, CN, $CO_2H$, $CF_3$, $NH_2$, $NO_2$, or di($C_1$–$C_4$) alkylamino; 2-, 3-, or 4-pyridinyl, pyrimidinyl; or biphenyl;

$R^4$ is H.

More specifically preferred because of biological activity are compounds of Formula (I) wherein:

D is N;

E is CH;

G is N;

x is S;

J is $C_2$–$C_{10}$ alkyl.

$R^1$ is selected from H, $CH_3$ or $NO_2$;

$R^2$ is $C_1$–$C_8$ alkyl, $C_3$–$C_8$ branched alkyl, $C_7$–$C_{14}$ araalkyl where the aryl group is optionally substituted with 1 to 3 groups selected from $CH_3$, $CH_3O$, F, $NH_2$, $NO_2$, or di($C_1$–$C_4$) alkylamino; phenyl optionally substituted with 1 to 3 groups selected from $CH_3$, $CH_3O$, F, $NH_2$, $NO_2$, or $di(C_1-C_4)$alkylamino; benzyl optionally substituted with 1 to 3 groups selected from $CH_3$, $CH_3O$, F, $NH_2$, $NO_2$, or $di(C_1-C_4)$alkylamino; 2-, 3-, or 4- pyridinyl, pyrimidinyl; or biphenyl;

$R^3$ is $C_1-C_8$ alkyl, $C_3-C_8$ branched alkyl, $C_7-C_{14}$ araalkyl where the aryl group is optionally substituted with 1 to 3 groups selected from $C_1-C_4$ alkyl or alkoxy, F, $NH_2$, $NO_2$, $C_1-C_4$ carboalkoxy, or $di(C_1-C_4)$ alkylamino; phenyl optionally substituted with 1 to 3 groups selected from $C_1-C_4$ alkyl or alkoxy, F, $NH_2$, $NO_2$, $C_1-C_4$ carboalkoxy, or $di(C_1-C_4)$alkylamino; benzyl optionally substituted with 1 to 3 groups selected from $C_1-C_4$ alkyl or alkoxy, F, $NH_2$, $NO_2$, $C_1-C_4$ carboalkoxy, or $di(C_1-C_4)$alkylamino; 2-, 3-, or 4- pyridinyl, pyrimidinyl; or biphenyl.

Specifically preferred are:

N'-(2,4-Difluorophenyl)-N-heptyl-N-[5-(9H-purin-6-ylthio) pentyl] urea

N'-(2,4-Difluorophenyl)-N-heptyl-N-[5-(1H-pyrazolo(3, 4-d)pyrimidin- 4-ylthio)pentyl]urea

DETAILED DESCRIPTION OF THE INVENTION

Synthesis

The novel compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the heterocycle and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternative methods described must then be used.

The compounds of Formula (6) where X is O, S, or NH, can be prepared by the route shown in Scheme 1. The compounds of Formula (1) can be prepared from a lactone or an hydroxyalkylcarboxylic acid ester of Formula (A) or (B), respectively, where J' is a moiety having one less methylene group than J, and an appropriate amine, neat or in an inert solvent such as N,N-dimethylformamide at ambient or elevated temperatures.

The amines of Formula (2) are prepared by reduction of the corresponding amide of Formula (1) by a variety of well known methods well known to those skilled in the art. For example, reagents such as lithium aluminum hydride, diborane, sodium bis(2-methoxyethoxy)aluminum hydride (Red-Al®), and diisobutylaluminum hydride can be used to reduce an amide to an amine. Such reactions are typically conducted in an appropriate anhydrous aprotic solvent such as ether, toluene or tetrahydrofuran at a temperature from room temperature to the boiling point of the solvent for a period of 2–48 hours.

The compounds of Formula (3) where Y is O and Z is $NR^4$, $OR^4$ or $R^4$, are prepared by the reaction of the secondary amines of Formula (1) with the requisite isocyanates, chloroformates, acid chlorides, activated ureas or activated carboxylic acid derivatives in an appropriate solvent such as hexane, toluene, diethyl ether, diphenyl ether, methylene chloride or tetrahydrofuran at a temperature at or below the boiling point of the solvent.

The guanidines of Formula (3) wherein Y is NH and Z is $NHR^4$, are prepared by the reaction of the secondary amines of Formula (1) with an appropriately substituted S-methyl carbamimidothioate salt (C. R. Rasmussen, F. J. Villani, et al., *Synthesis*, 460, 1988), in acetonitrile or dioxane at reflux.

The compounds of Formula (4) can be prepared by conversion of the hydroxy group to a halogen moiety by a variety of well known methods. Examples of these methods are phosphorous tribromide, phosphorous oxychloride, thionyl chloride, or triphenylphosphine and carbon tetrabromide. Or, compounds of Formula (4) where M is a tosylate or similar functionality, can be prepared from toluene sulfonyl chloride and triethylamine, in an appropriate aprotic solvent such as methylene chloride, tetrahydrofuran or toluene.

The compounds of Formula (6) can be prepared by converting the requisite compounds of Formula (5) where X is OH, SH or $NH_2$, into the corresponding alkali metal salt by addition of a base such as sodium hydride or potassium carbonate and alkylating with the compounds of Formula (4) in a polar aprotic solvent such as N,N-dimethylformamide or tetrahydrofuran at an appropriate temperature.

The compounds of Formula (6) wherein J is branched alkyl, can be prepared by a route analogous to that shown in Scheme 1. The requisite lactones with branching substituents can be prepared by functionalization of the parent unsubstituted lactones. Alternatively, branched cyclic α,ω-diacid anhydrides can be reduced to the corresponding branched lactone using agents such as sodium borohydride. Synthesis of compounds of Formula (4) then proceeds exactly as described in the preceding paragraph, and alkylation of compounds of Formula (5) affords compounds of Formula (6), wherein J is branched alkyl.

The amines of Formula (6) wherein Y is $H_2$, are prepared by reaction of the corresponding ureas or amides of Formula (6) wherein Y is O, with a reducing agent such as lithium aluminum hydride or other such reagents in an appropriate anhydrous aprotic solvent such as hexane, toluene, diethylether or tetrahydrofuran at temperatures at or below the boiling point of the solvent.

Scheme 1

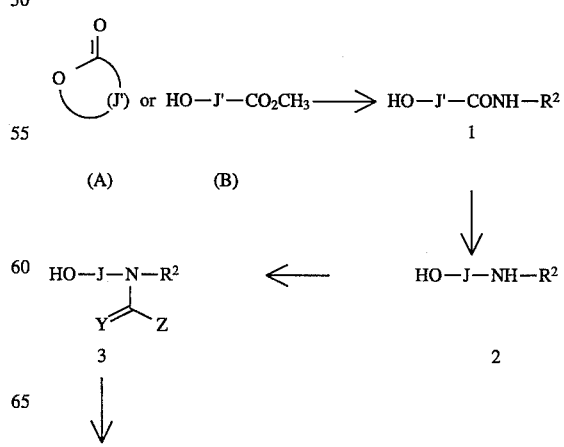

-continued
Scheme 1

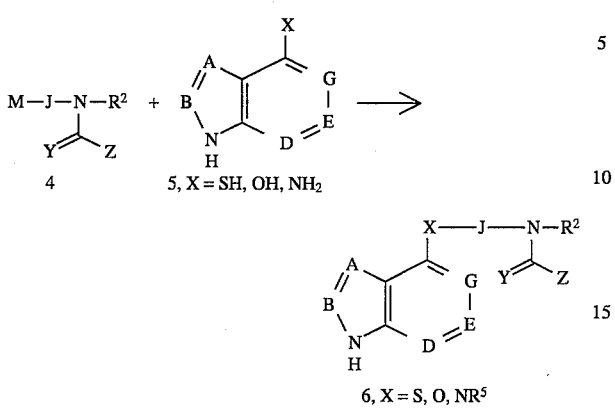

The compounds of Formula (5) wherein X is SH, OH or NH$_2$, Scheme 1, are available from commercial sources or can be prepared by methods which are well known in the chemical literature.

Alternately, the compounds of Formula (5) that are benzopyrroles of the structure

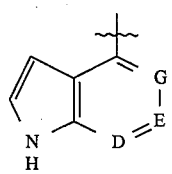

where D, E, and G are CR$^1$ and X is OH, SH or NH$_2$, Scheme 2, can be synthesized from the corresponding o-amino-ω-chlorostyrene of Formula (7) upon treatment with a base such as sodium ethoxide in a suitable solvent such as ethanol to give compounds of Formula (8).

Scheme 2

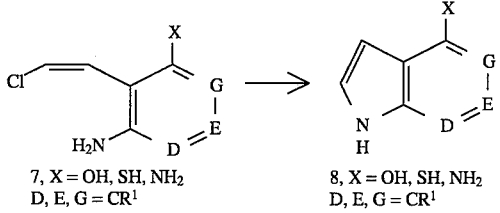

The compounds of Formula (1) that are benzopyrazoles or pyrazolopyridines of the structure

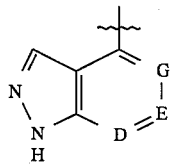

where D, E, and G are CR$^1$ or N with no more than one nitrogen per ring and X is OH, SH or NH$_2$, Scheme 3, can be synthesized upon heating of the corresponding o-hydrazinocinnamic acid of Formula (9) in a suitable solvent such as benzene to give compounds of Formula (10).

Scheme 3

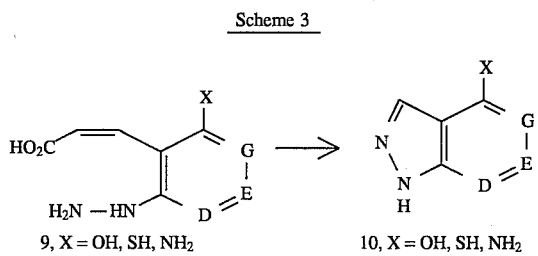

The compounds of Formula (5) that are benzimidazoles or imidazopyridines of the structure

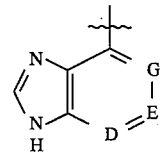

where D, E, and G are CR$^1$ or N with no more than one nitrogen per ring and X is OH, SH or NH$_2$, Scheme 4, can be synthesized upon heating of the corresponding o-phenylenediamine of formula (11) and formic acid in a suitable solvent such as N,N-dimethylformamide to give compounds of Formula (12).

Scheme 4

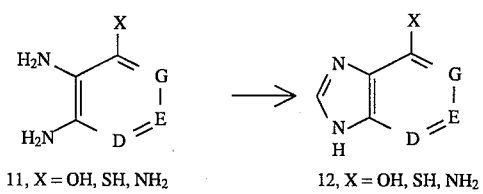

The compounds of Formula (5) that are pyrrolopyridines of the structure

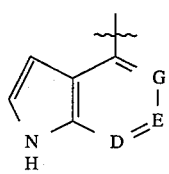

where D, E and G are CR$^1$ or N with no more than one nitrogen per ring and X is OH, SH or NH$_2$, Scheme 5, can be synthesized upon cyclization of the corresponding formamidomethylpicoline of Formula (13) using sodium anilide and potassium formate to give compounds of Formula (14).

Scheme 5

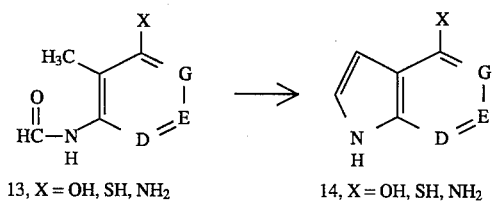

13, X = OH, SH, NH₂     14, X = OH, SH, NH₂

The compounds of Formula (5) that are pyrrolopyridazines of the structure

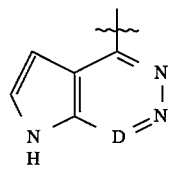

where D is CR¹ and X is OH, SH or NH₂, Scheme 6, can be synthesized upon heating of the corresponding 2-formyl-3-acylpyrole of Formula (15) with hydrazine to give compounds of Formula (16).

Scheme 6

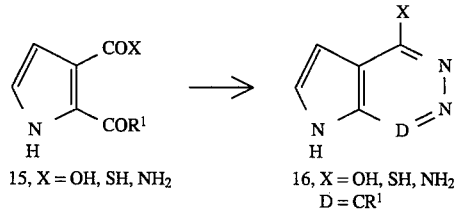

15, X = OH, SH, NH₂     16, X = OH, SH, NH₂
                                    D = CR¹

The compounds of Formula (5) that are pyrazolopyridazines of the structure

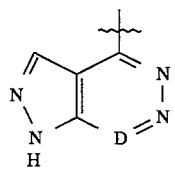

where D is CR¹ and X is OH, SH or NH₂, Scheme 7, can be synthesized upon heating the corresponding 5-chloro-4-hydroxymethylpyridazine of Formula (17) with hydrazine with subsequent treatment with nitrous acid to give compounds of Formula (18).

Scheme 7

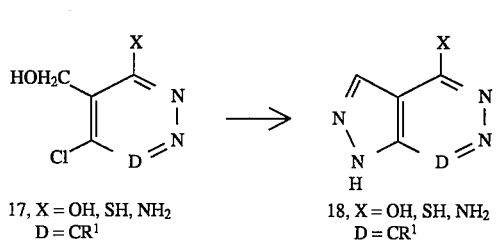

17, X = OH, SH, NH₂     18, X = OH, SH, NH₂
D = CR¹                       D = CR¹

The compounds of Formula (5) that are imidazopyridazines of the structure

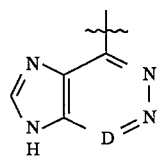

where D is CR¹ and X is OH, SH or NH₂, Scheme 8, can be synthesized upon heating of the corresponding pyridazinediamine of Formula (19) and formic acid in a suitable solvent such as N,N-dimethylformamide to give compounds of Formula (20).

Scheme 8

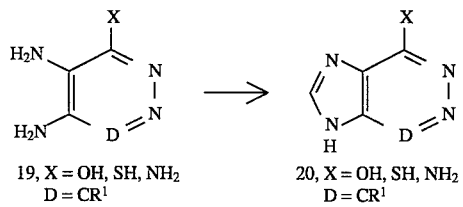

19, X = OH, SH, NH₂     20, X = OH, SH, NH₂
D = CR¹                       D = CR¹

The compounds of Formula (5) that are pyrrolopyrimidines of the structure

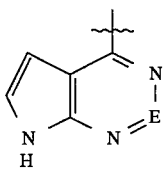

where E is CR¹ and X is OH, SH, NH₂, Scheme 9, can be synthesized from the corresponding o-amino-ω-chlorostyrene of Formula (21) upon treatment with a base such as sodium ethoxide in a suitable solvent such as ethanol to give compounds of Formula (22).

Scheme 9

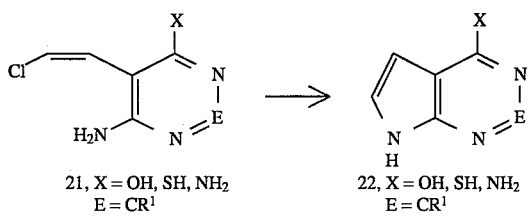

21, X = OH, SH, NH₂
E = CR¹

22, X = OH, SH, NH₂
E = CR¹

The compounds of Formula (5) that are pyrazolopyrimidines of the structure

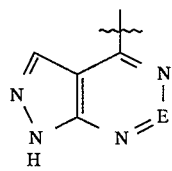

where E is CR¹ and X is OH, Scheme 10, can be synthesized from aminopyrazolocarboxyamide of Formula (23) and the appropriately substituted formamide of Formula (24) in a suitable solvent such as N,N-dimethylformamide to give compounds of Formula (25).

Scheme 10

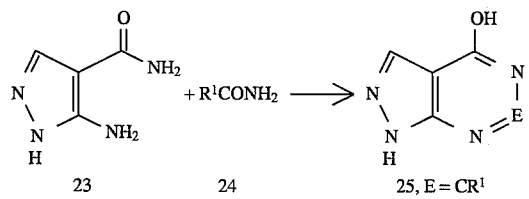

23     24     25, E = CR¹

The compounds of Formula (5) that are pyrazolopyrimidines of the structure

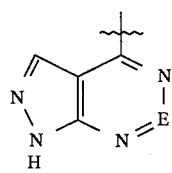

where E is CR¹ and X is SH, Scheme 11, can be synthesized from the corresponding 4-hydroxypyrazolopyrimidine of Formula (25) and phosphorous pentasulfide to give compounds of Formula (26).

Scheme 11

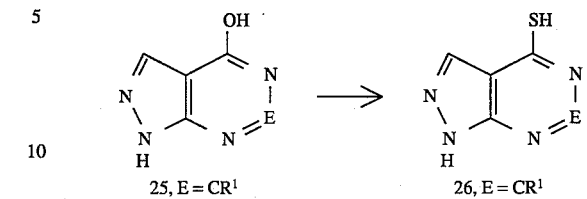

25, E = CR¹

26, E = CR¹

The compounds of Formula (5) that are pyrazolopyrimidines of the structure

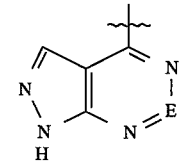

where E is CR¹ and X is NH₂, Scheme 12, can be synthesized from the corresponding 4-hydroxypyrazolopyrimidine of Formula (25) and phosphoryl chloride to give the corresponding 4-chloropyrazolopyrimidine of Formula (27) which is then treated with ammonia to give compounds of Formula (28).

Scheme 12

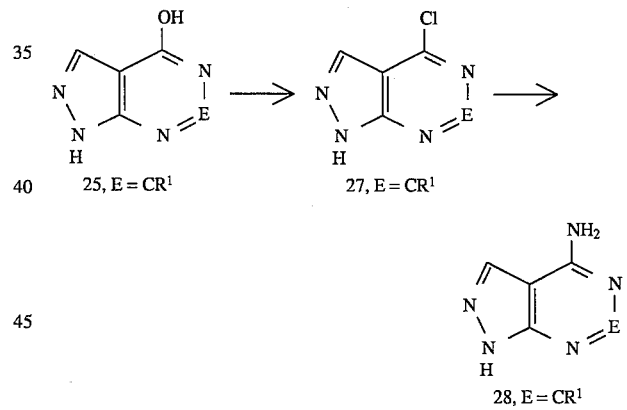

25, E = CR¹

27, E = CR¹

28, E = CR¹

The compounds of Formula (5) that are purines of the structure

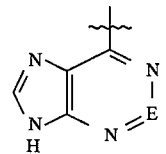

where E is CR¹ and X is OH or NH₂, Scheme 13, can be synthesized from the corresponding 4,5-diaminopyrimidines of Formula (29) and formic acid in a suitable solvent such as pyridine, N,N-dimethylformamide, or 1-propanol to give compounds of Formula (30).

Scheme 13

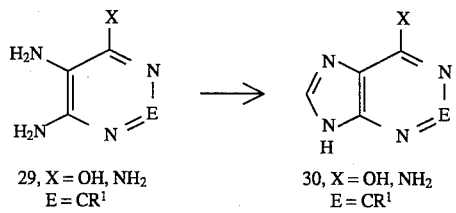

29, X = OH, NH₂
E = CR¹

30, X = OH, NH₂
E = CR¹

The compounds of Formula (5) that are purines of the structure

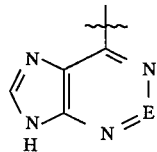

where E is CR¹ and X is SH, Scheme 14, can be synthesized from the corresponding 6-hydroxypurines of Formula (30) where X is O, and phosphorous pentasulfide in a suitable solvent such as benzene to give compounds of Formula (31).

Scheme 14

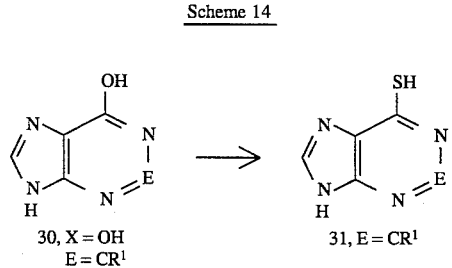

30, X = OH
E = CR¹

31, E = CR¹

The compounds of Formula (5) that are pyrrolopyridazines of the structure

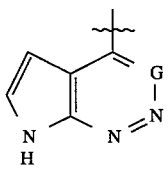

where G is CR¹ and X is OH, SH or NH₂, Scheme 15, can be synthesized from the corresponding 3-amino-ω-chlorostyrene of Formula (32) upon treatment with a base such as sodium ethoxide in a suitable solvent such as ethanol to give compounds of Formula (33).

Scheme 15

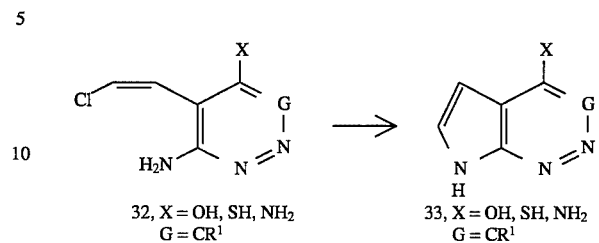

32, X = OH, SH, NH₂
G = CR¹

33, X = OH, SH, NH₂
G = CR¹

The compounds of Formula (5) that are pyrazolopyridazines of the structure

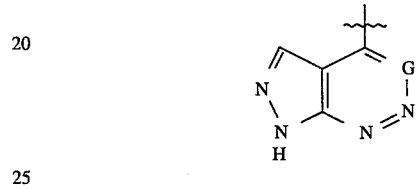

where G is CR¹ and X is OH, SH or NH₂, Scheme 16, can be synthesized upon heating the corresponding 3-chloro-4-hydroxymethylpyridazine of Formula (34) with hydrazine with subsequent treatment with nitrous acid to give compounds of Formula (35).

Scheme 16

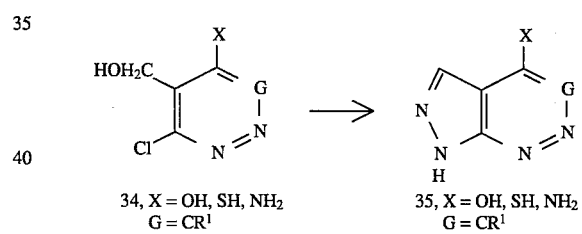

34, X = OH, SH, NH₂
G = CR¹

35, X = OH, SH, NH₂
G = CR¹

The compounds of Formula (5) that are imidazopyridazines of the structure

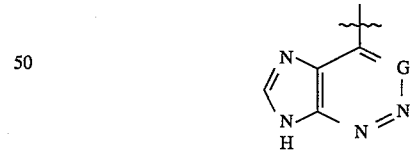

where G is CR¹ and X is OH, SH or NH₂, Scheme 17, can be synthesized upon heating of the corresponding pyridazinediamine of Formula (36) and formic acid in a suitable solvent such as N,N-dimethylformamide to give compounds of Formula (37).

Scheme 17

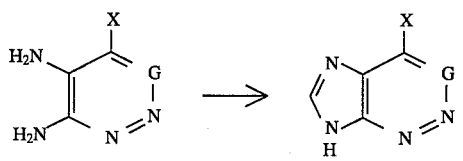

36, X = OH, SH, NH$_2$
G = CR$^1$

37, X = OH, SH, NH$_2$
G = CR$^1$

The compounds of Formula (6) wherein X is CH$_2$, can be prepared by the route shown in Scheme 18. The corresponding chloro-substituted compounds of Formula (38) can be converted to the cyano-substituted compounds of Formula (39) by treatment with as cuprous cyanide or sodium cyanide in a solvent such as dimethyl sulfoxide. This is a general reaction of a halide (Cl, Br, I) which involves nucleophilic substitution by a wide variety of substitutients (P. Herdewijin, *Synthesis*, 1989, 961). The nitriles of Formula (39) can be hydrolyzed to the corresponding carboxylic acid of Formula (40) upon heating in aqueous alkali or acid. The carboxylic acids of Formula (40) can be reduced to the corresponding alcohol of Formula (41) upon treatment with lithium aluminum hydride in an appropriate anhydrous aprotic solvent such as tetrahydrofuran or toluene at a temperature at or below the boiling point of the solvent. The alcohols of Formula (41) can be converted to the corresponding aldheyde upon treatment with potassium dichromate under acidic conditions to give compounds of Formula (42). The aldehydes of Formula (42) can be converted to the corresponding compounds of Formula (44) via the Wittig Reaction using an appropriate phosphoylide of Formula (43) prepared from the desired bromoalkylamine and triphenylphosphene. The compounds of Formula (44) can be converted to the corresponding compounds of Formula (45) via catalytic hydrogenation using a catalyst such as palladium on activated carbon in a solvent such as ethanol. The compounds of Formula (45) can be converted to the compounds of Formula (6) upon treatment with the requisite isocyanate, chloroformate, acid chloride or other activated carboxylic acid derivative as previously described.

Likewise, compounds of Formula (6) wherein X is O, S, NH or CH$_2$ and Y is H$_2$, can be prepared by reacting compounds similar to compounds of Formula (45) with an appropriately functionalized secondary amine HN(CH$_2$Z)R$^3$, in a solvent such as toluene, acetonitrile, tetrahydrofuran, or N,N-dimethylformamide at a temperature at or below the boiling point of the solvent.

Scheme 18

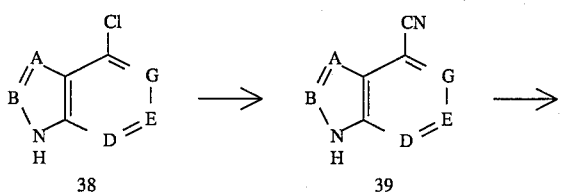

-continued
Scheme 18

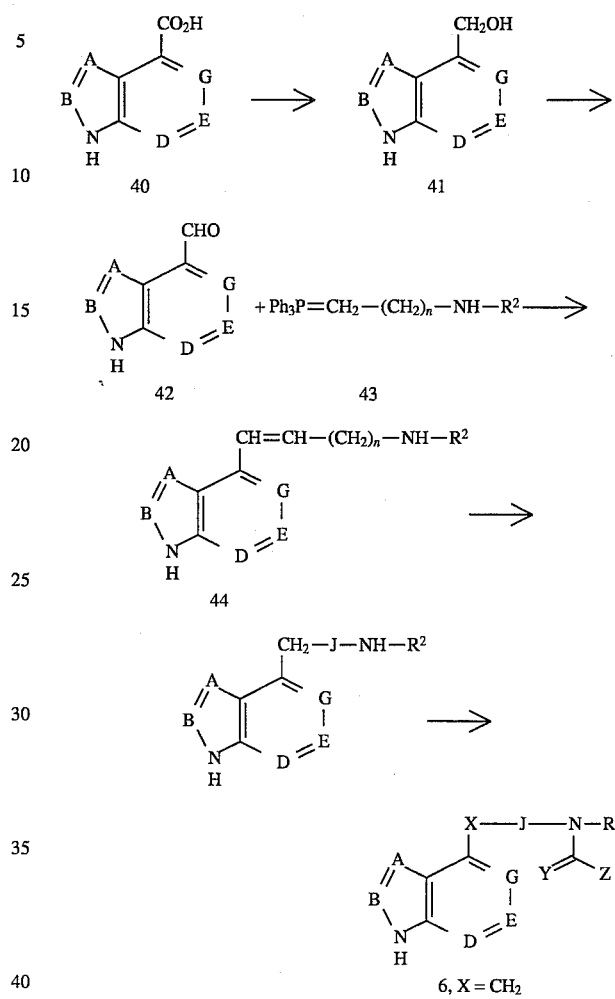

As shown in Scheme 19, the thioureas or thioamides of Formula (47) where Y is S and Z is NHR$^4$ or R$^4$, can be prepared from the corresponding ureas or amides of Formula (46) by the reaction with Lawesson's reagent or diphosphorus pentasulfide in an appropriate solvent such as toluene.

Scheme 19

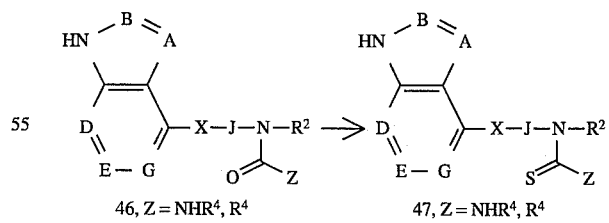

46, Z = NHR$^4$, R$^4$

47, Z = NHR$^4$, R$^4$

As shown in Scheme 20, the compounds of Formula (I) wherein X is S(O)$_r$ and r is 1 or 2, can be prepared by the oxidation of the compounds of Formula (48) by methods which are well known in the chemical literature. For example, the oxidation of compounds of Formula (48) with one equivalent of a peracid such as m-chloroperoxybenzoic acid in a suitable solvent such as methylene chloride at a low temperature affords primarily the sulfoxides of Formula (49), and the oxidation of compounds of Formula (48) with an oxidant such as potassium hydrogen persulfate, or Oxone®, in a suitable solvent such as methanol affords the sulfones of Formula (50).

Scheme 20

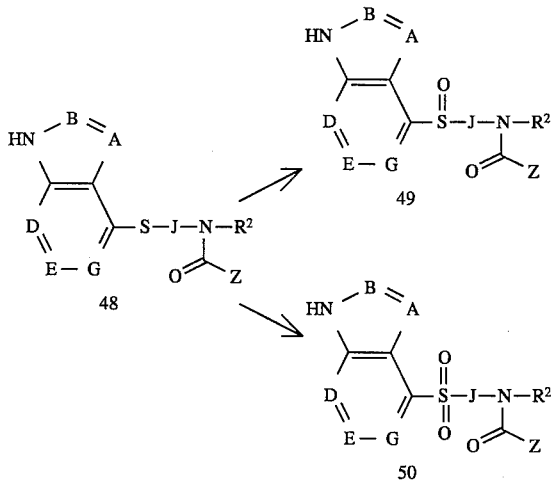

Preparation of pharmaceutically suitable salts of Formula (I) can be carried out in accordance with well known techniques for forming salts. Physiologically acceptable salts include acid addition salts, e.g., hydrochloric, sulfuric, acetic, trifluoroacetic, succinic, citric, and benzene sulfonic acid salts.

The compounds of this invention and their preparation can be further understood by the following examples, which exemplify but do not constitute a limitation of the invention. In these examples, unless otherwise indicated, all temperatures are in degrees centigrade and parts and percentages are by weight.

EXAMPLE 1

Preparation of
N'-(2,4-difluorophenyl)-N-heptyl)-N-[5-(9H-purin-6-ylthio)pentyl] urea Part A. A solution of γ-valerolactone (25.0 g, 0.249 mol) in toluene (50 mL) and n-heptylamine (35.96 g, 0.312 mol) was heated to reflux for 18 hours under a nitrogen atmosphere. The reaction mixture was allowed to cool to ambient temperature, diluted with ethyl acetate (300 mL), washed with 1 N aqueous HCl (50 mL), water and brine. The organic layer was dried over magnesium sulfate and concentrated to give a white solid. The product was crystallized from ethyl ether:hexane to give N-heptyl-5-hydroxypentanamide (41.8 g, 0.194 mol) as white plates, mp 55°–56°. $^1$H NMR (CDCl$_3$) δ6.06 (bs, 1H), 3.61 (t,2H, J=7.3 Hz), 3.24 (quartet, 2H,J=8.4 Hz), 3.19 (bs, 1H), 2.19 (t,2H, J=8.3 Hz), 1.80–1.23 (m, 14H), 0.86 (t,3H, J=6.0 Hz).

Part B. To a solution of lithium aluminum hydride (6.7 g, 0.176 mol) in dry tetrahydrofuran (300 mL), a solution of N-heptyl-5-hydroxypentanamide (19.0 g, 0.088 mol) in dry tetrahydrofuran (100 mL) under a nitrogen atmosphere was added dropwise. The reaction mixture was heated to reflux for 18 hours, allowed to cool to room temperature and was poured slowly into a stirred mixture of 10% aqueous sodium sulfate (400 mL) and ice (200 mL). The resulting slurry was filtered through a bed of Celite® and the filtrate was extracted with ethyl acetate (2×500 mL). The combined organic extracts were washed with water and brine, then dried over magnesium sulfate and concentrated to give a viscous yellow oil. The product was crystallized from hexane to give N-(5-hydroxypentyl)-N-heptylamine (15.2 g, 0.075 mol) as a white powder, mp 47°–48°. $^1$H NMR (CDCl$_3$) δ 3.63 (t,2H, J=8.4 Hz), 2.63 (quartet,4H,J=8.3 Hz), 2.39 (bs,2H), 1.66–1.24 (m, 16H), 0.91 (t,3H,J=6.6 Hz).

Part C. To a solution of N-(5-hydroxypentyl)-N-heptylamine (11.65 g, 0.0578 mol) in methylene chloride (75 mL) under a nitrogen atmosphere cooled to 0°, 2,4-difluorophenylisocyanate (8.97 g, 0. 0578 mol) was added slowly. The reaction mixture was stirred for 1 hour, poured into 1 N aqueous HCl (200 mL) and extracted with ethyl acetate (300 mL). The combined organic extracts were washed with water and brine, then dried over magnesium sulfate and was concentrated to give N'-{2,4-difluorophenyl)-N-heptyl-N-5-hydroxypentylurea as a pale yellow oil (20.0 g, 0.056 mol). $^1$H NMR (CDCl$_3$) δ8.03 (m, 1H), 6.88–6.59 (m, 2H), 6.45 (bs, 1H), 3.68 (t, 2H, J=8.4 Hz), 3.33 (m, 4H), 1.81–1.22 (m, 16H), 0.91 (t,3H, J=6.7 Hz).

Part D. To a solution of N'-(2,4-difluorophenyl) -N-heptyl-N- 5-hydroxypentylurea (15.0 g, 0.042 mol) and carbon tetrabromide (16.75 g, 0.051 mol) in methylene chloride (350 mL) under a nitrogen atmosphere at ambient temperature, a solution of triphenylphosphine ( 13.24 g, 0.051 mol) in methylene chloride (100 mL) was added slowly. The reaction mixture was stirred for 3 hours and then concentrated in vacuo to give crude viscous oil. The product was purified by flash chromatography on silica gel (400 mL) eluting with hexane:ethyl acetate (90:10::v:v) to give N-(5-bromopentyl)-N' -(2,4-difluorophenyl)-N-heptylurea as a viscous colorless oil (17.5 g, 0.042 mol). $^1$H NMR (CDCl$_3$) δ8.14–8.00 (m, 1H), 6.92–6.79 (m, 2H), 6.35 (bs, 1H), 3.49–3.25 (m, 6H), 1.99–1.26 (m, 16H), 0.92 (t,3H, J=6.7 Hz).

Part E. To a suspension of sodium hydride (0.04 g, 60% mineral oil dispersion, 0.001 mol; washed free of mineral oil with hexane) and sodium iodide (0.04 g, 0.0003 mol) in N,N-dimethylformamide (10 mL) under a nitrogen atmosphere, cooled to 0°, a solution of 6-mercaptopurine monohydrate (0.17 g, 0.001 mol) in N,N-dimethylformamide (5 mL) was added slowly. The reaction mixture was stirred for 30 minutes and then a solution of N-(5-bromopentyl)-N'-( 2,4-difluorophenyl)-N-heptylurea (0.42 g, 0.001 mol) in N,N-dimethylformamide (5 mL) was added. The reaction mixture was stirred for 30 minutes and then allowed to warm to ambient temperature and stirred an additional 120 hours. The reaction mixture was poured into water (50 mL) and extracted with ethyl acetate (2×50 mL). The combined organic extracts were washed with water and brine, then dried over magnesium sulfate and concentrated to give a viscous oil. The product was purified by flash chromatography on silica gel eluting with hexane:ethyl acetate (50:50::v:v) to give the title compound (0.31 g, 0.00063 mol) as a pure white solid, mp= 87°–89°. $^1$H NMR (CDCl$_3$) δ8.9 (s, 1H), 8.2 (s,1H), 8.1–8.0 (m, 1H), 6.9–6.8 (m, 2H), 6.5 (s, 1H), 3.5–3.2 (m, 6H), 1.9–1.2 (m, 17H), 0.9– 0.8 (m, 3H).

EXAMPLE 2

Preparation of
N'-(2,4-difluorophenyl)-N-heptyl-N-[5-(1H-pyrazolo
(3,4-d)pyrimidin-4-ylthio)pentyl]urea Employing the method of Example 1, Part E, but using 4-mercapto-1-pyrazolopyrimidine (0.15 g, 0.001 mol), the title compound (0.39 g, 0.00079 mol) was isolated as a viscous oil. $^1$H NMR (CDCl$_3$) δ8.75 (s, 1H), 8.1–8.0 (m, 2H), 7.9–7.8 (m, 2H), 6.5–6.4 (m, 1H), 3.4–3.2 (m, 6H), 1.9–1.2 (m, 18H), 0.9–0.8 (m, 3H).

EXAMPLE 3

Preparation of
N-heptyl-N'-(1-methylethyl)-N-[5-(9H-purin-
6-ylthio)pentyl] urea To a solution of 2-mercaptopurine monohydrate (0.41 g, 0.0024 mol) and potassium carbonate (0.33 g, 0.0024 mol) and sodium iodide (0.03 g) in dry tetrahydrofuran (10 mL) was added, dropwise, a solution of N-(5-bromopentyl)-N'-(1-methylethyl)-N-heptylurea (0.84 g, 0.0024 mol) in dry tetrahydrofuran (5 mL). The reaction mixture was stirred at 55°–60° for 20 hours. The reaction mixture was poured into water and extracted with ethyl acetate. The organic layer was dried over magnesium sulfate and concentrated. The residue was purified by flash chromatography using ethyl acetate to give the title compound (0.56 g, 0.0013 mol) as a clear, viscous oil. $^1$H NMR (CDCl$_3$) δ8.75 (s, 1H), 8.2 (s, 1H), 4.2–3.9 (m, 2H), 3.5–3.3 (m, 2H), 3.3–3.1 (m, 4H), 1.9–1.1 (m, 23H), 0.9–0.8 (m, 3H).

EXAMPLE 4

Preparation of
N-heptyl-N'-(1-methylethyl)-N-[5-(1H-pyrazolo
(3,4-d)pyrimidin-4-ylthio)pentyl]urea Employing the method of Example 3, but using 4-mercapto-1-pyrazolopyrimidine (0.37 g; 0.0024 mol), the title compound (0.70 g, 0.0017 mol) was isolated as a pale yellow solid, mp= 81°–83°. $^1$H NMR (CDCl$_3$) δ8.8 (s, 1H), 8.1 (s, 1H), 4.1–3.9 (m, 2H), 3.4 (t, 2H, J=7.4Hz), 3.2 (t,2H, J=6.3Hz), 3.1 (t,2H, J=7.5Hz), 1.8 (quintet,2H, J=7.3Hz), 1.7–1.2 (m, 15H), 1.15 (d, 6H,J=6.3Hz), 0.9 (t, 3H, J=6.1Hz).

EXAMPLE 5

Preparation of phenyl
N-[5-(9H-purin-6-ylthio)pentyl]-N-heptylcarbamate

Employing the method of Example 3, but using phenyl N-(5-bromopentyl)-N-heptylcarbamate (0.92 g, 0.0024 mol), the title compound (0.48 g, 0.0011 mol) was isolated as an oil. $^1$H NMR (CDCl$_3$) δ12.15 (bs, 1H), 8.75 (s, 1H), 8.1 (s,1H), 7.4–7.3 (m, 2H), 7.2–7.0 (m, 3H), 3.5–3.2 (m, 7H), 1.95–1.2 (m, 15H), 0.9–0.8 (m, 3H).

EXAMPLE 6

Preparation of phenyl
N-[5-(1H-pyrazolo(3,4-d)pyrimidin-
4-ylthio)pentyl]-N-heptylcarbamate Employing the method of Example 5, but using 4-mercapto- 1-pyrazolopyrimidine (0.37 g, 0.0024 mol), the title compound (1.10 g, 0.0024 mol) was isolated as a clear yellow oil. $^1$H NMR (CDCl$_3$) δ12.0 (bs, 1H), 8.8 (s, 1H), 8.15 (s, 1H), 7.4–7.05 (m, 5H), 3.5–3.25 (m, 6H), 1.95–1.45 (m, 8H), 1.4–1.2 (m, 8H), 0.85 (t, 3H, J=6.6Hz).

TABLE 1

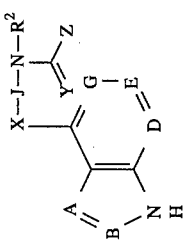

| EX. | A | B | D | E | G | X | J | R³ | Y | Z | Data (mp °C.) |
|---|---|---|---|---|---|---|---|---|---|---|---|
| 1 | N | CH | N | CH | N | S | $CH_2(CH_2)_3CH_2$ | $(CH_2)_6CH_3$ | O | NH-2,4-diF—$C_6H_3$ | 87-89 |
| 2 | CH | N | N | CH | N | S | $CH_2(CH_2)_3CH_2$ | $(CH_2)_6CH_3$ | O | NH-2,4-diF—$C_6H_3$ | oil[a] |
| 3 | CH | CH | N | CH | N | S | $CH_2(CH_2)_3CH_2$ | $(CH_2)_6CH_3$ | O | NH—$CH(CH_3)_2$ | oil[b] |
| 4 | CH | N | N | CH | N | S | $CH_2(CH_2)_3CH_2$ | $(CH_2)_6CH_3$ | O | NH—$CH(CH_3)_2$ | 81-83 |
| 5 | N | CH | N | CH | N | S | $CH_2(CH_2)_3CH_2$ | $(CH_2)_6CH_3$ | O | O—$C_6H_5$ | oil[c] |
| 6 | CH | CH | N | CH | N | S | $CH_2(CH_2)_3CH_2$ | $(CH_2)_6CH_3$ | O | O—$C_6H_5$ | oil[d] |
| 7 | N | CH | N | CH | N | SO | $CH_2CH(CH_3)(CH_2)_3$ | $CH_3$ | S | NH-2,4-diOH—$C_6H_3$ | |
| 8 | N | CH | N | CH | N | $SO_2$ | $(CH_2)_3CH(CH_3)CH_2$ | $CH_2CH(CH_3)_2$ | $H_2$ | NH-4-CN—$C_6H_4$ | |
| 9 | N | CH | $CF_3$—C | F—C | N | S | $(CH_2)_3CH(C_5H_{11})(CH_2)_4$ | $CH_2$—$C_6H_{11}$ | NH | NH-2,4,6-tri$CF_3$—$C_6H_2$ | |
| 10 | N | CH | N | $CH_3O$—C | N | S | $(CH_3)_3(CH_2)$ | $CH_2CH_2$—$C_6H_5$ | O | $CH_2CH(CH_3)_2$ | |
| 11 | N | $CF_3$—C | N | CH | N | S | $CH_2CH=CH(CH_2)_2$ | 2,4-diF—$C_6H_3$ | O | $CH_2$—$C_6H_{11}$ | |
| 12 | N | CN—C | N | CH | N | O | $CH_2CH=CH(CH_2)_2$ | $CH_2CH=CH(CH_2)_2CH_3$ | O | $CH_2$-2,6-diCH$(CH_3)_2$—$C_6H_3$ | |
| 13 | N | $CH_3S$—C | N | CH | N | NH | $(CH_2)_3CH=CH(CH_2)_2$ | $CH_2C≡C(CH_2)_2CH_3$ | O | O—$(CH_2)_7CH_3$ | |
| 14 | N | CH | N | CH | N | $CH_2$ | $CH_2C≡C(CH_2)_2$ | $CH_2$-2,4-diOH—$C_6H_4$ | S | O—$CH_2$—$C_6H_{11}$ | |
| 15 | N | CH | N | $(CH_3)_2CH$—C | N | SO | $(CH_2)_4C≡C(CH_2)_2$ | 4-$CH_3O$—$C_6H_4$ | S | O—$CF_2CF_3$ | |
| 16 | N | CH | N | CH | N | NH | $CH_2(CH_2)_4CH_2$ | 2,4,6-tri$CF_3$—$C_6H_2$ | $H_2$ | NH—$(CH_2)_2$—$C_6H_5$ | |
| 17 | CH | N | N | CH | N | S | $CH_2CH(CH_3)(CH_2)_3$ | $CH_2$-4-pyridinyl | S | $CH_2C≡C(CH_2)_2CH_3$ | |
| 18 | $CH_3S$—C | N | N | CH | N | S | $CH_2CH=CH(CH_2)_2$ | $CH_3$ | O | $CH_2$—$C_6H_5$ | |
| 19 | CH | CH | N | CH | N | SO | $CH_2CH=CH(CH_2)_2$ | $CH_2CH(CH_3)_2$ | O | $C_6H_5$ | |
| 20 | CH | CH | N | CH | N | S | $CH_2C≡C(CH_2)_2$ | $CH_2$—$C_6H_5$ | S | $CH_2$—$C_6H_5$ | |
| 21 | $CH_3(CH_2)_7$—C | N | N | CH | N | $SO_2$ | $(CH_2)_3C≡C(CH_2)_2$ | $CH_2CH_2$—$C_6H_5$ | S | O—$CH(CH_3)_2$ | |
| 22 | N | N | N | CH | N | $SO_2$ | $CH_2(CH_2)_3CH_2$ | $CH_2$-4-$CO_2H$—$C_6H_4$ | O | NH-3-pyridinyl | |
| 23 | $CH_3CH_2$—O—C | CH | F—C | N | N | S | $CH_2(CH_2)_3CH_2$ | 2,4,6-tri$CF_3$—$C_6H_2$ | O | $CH_2$-2,4,6-tri$CH_3O$—$C_6H_2$ | |
| 24 | N | CH | $CH_3$—C | N | N | SO | $CH_2(CH_2)_3CH_2$ | $CH_2$-4-$CO_2H$—$C_6H_4$ | O | NH-3-pyridinyl | |
| 25 | N | CH | CH | CH | N | $SO_2$ | $CH_2(CH_2)_3CH_2$ | 2,6-di$CH_3O$—$C_6H_3$ | O | $CH_3$-2-pyrimidinyl | |
| 26 | N | CN—C | CH | CH | N | S | $CH_2(CH_2)_3CH_2$ | $CH_3$ | O | NH-2,4-diOH—$C_6H_3$ | |
| 27 | N | CH | CH | CH | N | SO | $(CH_2)_3CH(CH_3)CH_2$ | $CH_2CH(CH_3)_2$ | S | NH-4-CN—$C_6H_4$ | |
| 28 | N | CH | CH | CH | N | S | $CH(CH_3)(CH_2)_4$ | $CH_3$ | S | $CH_2$—$C_6H_{11}$ | |
| 29 | N | CH | CH | N | N | SO | $CH_2CH=CH(CH_2)_2$ | 2,4-diF—$C_6H_3$ | O | $CH_2$-2,6-diCH$(CH_3)_2$—$C_6H_3$ | |
| 30 | N | CH | CH | N | N | $SO_2$ | $(CH_2)_3CH=CH(CH_2)_2$ | $CH_2C≡C(CH_2)_2CH_3$ | O | O—$(CH_2)_7CH_3$ | |
| 31 | N | CH | CH | N | N | S | $CH_2C≡C(CH_2)_2$ | $CH_2$-2,4-diOH—$C_6H_3$ | S | O—$CH_2$—$C_6H_{11}$ | |
| 32 | N | $NH_2$—C | CH | N | N | SO | $(CH_2)_3C≡C(CH_2)_2$ | 4-$CH_3O$—$C_6H_4$ | S | O—$CF_2CF_3$ | |

TABLE 1-continued

| EX. | A | B | D | E | G | X | J | R³ | Y | Z | Data (mp °C.) |
|-----|---|---|---|---|---|---|---|----|---|---|---|
| 33 | CH | N | CH₃—C | N | N | S | CH₂(CH₂)₆CH₂ | CH₂-4-(CH₃)₂N—C₆H₄ | O | CH₂-4-(CH₃)₂N—C₆H₄ | |
| 34 | CH | N | CH | N | N | S | CH₂(CH₂)₂CH₂ | CH₂(CH₂)₂CH₂ | O | CH₂CH=CH(CH₂)₂CH₃ | |
| 35 | CH | N | CH | N | N | SO | CH₂(CH₂)₈CH₂ | CH₂(CH₂)₂CH₂ | S | O—C₆H₅ | |
| 36 | CH | N | CH | N | N | S | CH₂CH(CH₃)(CH₂)₃ | CH₂CH(CH₃)(CH₂)₃ | | CH₂C≡C(CH₂)₂CH₃ | |
| 37 | CH | N | CH | N | N | S | CH₂CH=CH(CH₂)₂ | CH₃ | O | CH₂—C₆H₅ | |
| 38 | CH | N | CH | N | N | SO | (CH₂)₃CH=CH(CH₂)₂ | CH₂CH(CH₃)₂ | O | C₆H₅ | |
| 39 | NH₂—C | N | CH | N | N | SO₂ | CH₂C≡C(CH₂)₂ | CH₂—C₆H₁₁ | S | CH₂—C₆H₅ | |
| 40 | N | N | N | N | F—C | SO₂ | CH₂(CH₂)₆CH₂ | CH₂(CH₂)₆CH₂ | O | CH₂-2,4,6-triCH₃O—C₆H₂ | |
| 41 | N | CN—C | N | N | CH | S | CH₂CH(CH₃)(CH₂)₃ | CH₃ | O | NH-2,4-diOH—C₆H₃ | |
| 42 | N | CH₃(CH₂)₇—C | N | N | CH | S | (CH₂)₃CH(CH₃)CH₂ | CH₂CH(CH₃)₂ | S | NH-4-CN—C₆H₄ | |
| 43 | N | CH | N | N | CH | SO | CH(CH₃)₂(CH₂)₄ | 2,4-diF—C₆H₃ | O | CH₂—C₆H₁₁ | |
| 44 | N | CH | N | N | CH | SO₂ | CH₂CH=CH(CH₂)₂ | CH₂CH=CH(CH₂)₂CH₃ | O | CH₂-2,6-diCH(CH₃)₂—C₆H₃ | |
| 45 | N | CH | N | N | CH | S | (CH₂)₃CH=CH(CH₂)₂ | CH₂C≡C(CH₂)₂CH₃ | O | O—(CH₂)₇CH₃ | |
| 46 | N | CH | N | N | CH | SO | CH₂C≡(CH₂)₂ | CH₂-2,4-diOH—C₆H₃ | S | O—CH₂—C₆H₁₁ | |
| 47 | N | CH | N | N | NH₂—C | SO | (CH₂)₃C≡C(CH₂)₂ | 4-CH₃O—C₆H₄ | S | O—CF₂CF₃ | |
| 48 | CH | N | N | N | CH₃—C | SO | CH₂(CH₂)₆CH₂ | CH₂-4-(CH₃)₂N—C₆H₄ | O | CH₂-4-(CH₃)₂N—C₆H₄ | |
| 49 | CH₃O—C | N | N | N | CH | SO₂ | CH₂(CH₂)₂CH₂ | CH₂-3-pyridinyl | O | CH₂CH=CH(CH₂)₂CH₃ | |
| 50 | CH | N | N | N | CH | SO | CH₂(CH₂)₈CH₂ | CH₂-2-pyrimidinyl | S | O—C₆H₅ | |
| 51 | CH | N | N | N | CH | S | CH₂CH(CH₃)(CH₂)₃ | CH₂-4-pyridinyl | S | CH₂C≡C(CH₂)₂CH₃ | |
| 52 | CH | N | CH | CH | CH | SO₂ | CH₂CH=CH(CH₂)₂ | CH₃ | O | CH₂—C₆H₅ | |
| 53 | CH | N | CH | CH | CH | SO | (CH₂)₃CH=CH(CH₂)₂ | CH₂CH(CH₃)₂ | O | C₆H₅ | |
| 54 | CH | N | CH | CH | NH₂—C | S | CH₂C≡C(CH₂)₂ | CH₂—C₆H₁₁ | S | CH₂—C₆H₅ | |
| 55 | CH | N | N | CH | CH | SO₂ | (CH₂)₃C≡C(CH₂)₂ | CH₂CH₂—C₆H₅ | S | O—CH(CH₃)₂ | |
| 56 | N | CH | N | N | CH | S | CH₂(CH₂)₆CH₂ | 2,4,6-triCF₃—C₆H₂ | O | CH₂-2,4,6-triCH₃O—C₆H₂ | |
| 57 | N | CH | CH | N | CH | SO₂ | CH₂(CH₂)₈CH₂ | 2,6-diCH₃O—C₆H₃ | O | CH₂-2-pyrimidinyl | |
| 58 | N | CH | CH | N | CH | S | CH₂CH(CH₃)(CH₂)₃ | CH₃ | O | NH-2,4-diOH—C₆H₃ | |
| 59 | N | CH | CH | N | CH | SO | (CH₂)₃CH(CH₃)CH₂ | CH₂CH(CH₃)₂ | O | NH-4-CN—C₆H₄ | |
| 60 | N | CH | CH | N | N | S | CH(CH₃)(CH₂)₄ | 2,4-diF—C₆H₃ | O | CH₂—C₆H₁₁ | |
| 61 | N | CH | CH | N | N | SO | CH₂CH=CH(CH₂)₂ | CH₂CH=CH(CH₂)₂CH₃ | O | CH₂-2,6-diCH(CH₃)₂—C₆H₃ | |
| 62 | N | CH | CH | N | N | S | (CH₂)₃CH=CH(CH₂)₂ | CH₂C≡C(CH₂)₂CH₃ | O | O—(CH₂)₇CH₃ | |
| 63 | CH | N | N | CH | CH | SO₂ | CH₂C≡C(CH₂)₂ | CH₂-2,4-diOH—C₆H₃ | S | O—CH₂—C₆H₁₁ | |

TABLE 1-continued

| EX. | A | B | D | E | G | X | J | R³ | Y | Z | Data (mp °C.) |
|---|---|---|---|---|---|---|---|---|---|---|---|
| 64 | CH | N | N | CH | CH | SO | (CH₂)₃C≡C(CH₂)₂ | 4-CH₃O—C₆H₄ | S | O—CF₂CF₂CF₃ | |
| 65 | CH | N | CH | N | CH | SO₂ | CH₂(CH₂)₆CH₂ | CH₂-4-(CH₃)₂N—C₆H₄ | O | CH₂-4-(CH₃)₂N—C₆H₄ | |
| 66 | CH | N | CH | N | CH | S | CH₂(CH₂)₇CH₂ | CH₂-3-pyridinyl | O | CH₂CH=CH(CH₂)₂CH₃ | |
| 67 | CH | N | CH | N | N | SO | CH₂(CH₂)₈CH₂ | CH₂-2-pyrimidinyl | S | O—C₆H₅ | |
| 68 | CH | N | CH | CH | N | S | CH₂CH(CH₃)(CH₂)₃ | CH₂-4-pyridinyl | S | CH₂C≡C(CH₂)₂CH₃ | |
| 69 | CH | N | CH | CH | CH | SO₂ | CH₂CH=CH(CH₂)₂ | CH₃ | O | CH₂—C₆H₅ | |
| 70 | CH | N | CH | CH | CH | SO | (CH₂)₃CH=CH(CH₂)₂ | CH₂CH(CH₃)₂ | O | C₆H₅ | |
| 71 | N | CH | CH | CH | CH | S | CH₂C≡C(CH₂)₂ | CH₂—C₆H₁₁ | S | CH₂—C₆H₅ | |
| 72 | N | CH | CH | CH | CH | SO₂ | (CH₂)₃C≡C(CH₂)₂ | CH₂—C₆H₅ | S | O—CH(CH₃)₂ | |
| 73 | CH | CH | N | CH | N | SO | CH₂(CH₂)₆CH₂ | 2,4,6-triCF₃—C₆H₂ | O | CH₂-2,4,6-triCH₃O—C₆H₂ | |
| 74 | CH | CH | N | CH | N | S | CH₂(CH₂)₇CH₂ | CH₂-4-CO₂H—C₆H₄ | O | NH-3-pyridinyl | |
| 75 | CH | CH | N | N | N | SO₂ | CH₂(CH₂)₈CH₂ | 2,6-diCH₃O—C₆H₃ | O | NH-2-pyrimidinyl | |
| 76 | CH | CH | N | N | N | SO | CH₂CH(CH₃)(CH₂)₃ | CH₃ | O | NH-2,4-diOH—C₆H₃ | |
| 77 | CH | CH | CH | N | N | S | CH(CH₃)(CH₂)₄ | CH₂CH(CH₃)₂ | S | NH-4-CN—C₆H₄ | |
| 78 | CH | CH | CH | N | N | SO | CH₂CH=CH(CH₂)₂ | 2,4-diF—C₆H₃ | O | CH₂—C₆H₅ | |
| 79 | CH | CH | N | N | CH | S | (CH₂)₃CH=CH(CH₂)₂ | CH₂CH=(CH₂)₂CH₃ | O | CH₂-2,6-diCH(CH₃)₂—C₆H₃ | |
| 80 | CH | CH | N | N | CH | S | (CH₂)₂CH=CH(CH₂)₂ | CH₂C≡C(CH₂)₂CH₃ | O | O—(CH₂)₇CH₃ | |
| 81 | CH | CH | N | N | CH | SO₂ | CH₂C≡C(CH₂)₂ | CH₂-2,4-diOH—C₆H₃ | S | O—CH₂—C₆H₁₁ | |
| 82 | CH | CH | N | CH | CH | SO | (CH₂)₃C≡C(CH₂)₂ | 4-CH₃O—C₆H₄ | S | O—CF₂CF₂CF₃ | |
| 83 | CH | CH | CH | N | CH | SO₂ | CH₂(CH₂)₆CH₂ | CH₂-4-(CH₃)₂N—C₆H₄ | O | CH₂-4-(CH₃)₂N—C₆H₄ | |
| 84 | CH | CH | CH | N | CH | S | CH₂(CH₂)₇CH₂ | CH₂-3-pyridinyl | O | CH₂CH=CH(CH₂)₂CH₃ | |
| 85 | CH | CH | CH | N | N | SO | CH₂(CH₂)₈CH₂ | CH₂-2-pyrimidinyl | S | O—C₆H₅ | |
| 86 | CH | CH | CH | CH | N | S | CH₂CH(CH₃)(CH₂)₃ | CH₂-4-pyridinyl | S | CH₂C≡C(CH₂)₂CH₃ | |
| 87 | CH | CH | CH | CH | CH | S | CH₂CH=CH(CH₂)₂ | CH₃ | O | CH₂—C₆H₅ | |
| 88 | CH | CH | CH | CH | CH | SO₂ | (CH₂)₃CH=CH(CH₂)₂ | CH₂CH(CH₃)₂ | O | C₆H₅ | |

Footnotes To Table 1
(a) ¹H NMR (CDCl₃) δ 8.75 (s,1H), 8.1–8.0 (m,2H), 7.9–7.8 (m,2H), 6.5–6.4 (m,1H), 3.4–3.2 (m,6H), 1.9–1.2 (m,18H), 0.9–0.8 (m,3H).
(b) ¹H NMR (CDCl₃) δ 8.75 (s,1H), 8.2 (s,1H), 8.75 (s,1H), 4.2–3.9 (m,2H), 3.5–3.35 (m,2H), 3.3–3.1 (m,4H), 1.9–1.1 (m,23H), 0.9–0.8 (m,3H).
(c) ¹H NMR (CDCl₃) δ 12.15 (bs,1H), 8.75 (s,1H), 8.1 (s,1H), 7.4–7.3 (m,2H), 7.2–7.0 (m,3H), 3.5–3.2 (m,7H), 1.95–1.2 (m,15H), 0.9–0.8 (m,3H).
(d) ¹H NMR (CDCl₃) δ 12.0 (bs,1H), 8.8 (s,1H), 8.15 (s,1H), 7.4–7.05 (m,5H), 3.5–3.25 (m,6H), 1.95–1.45 (m,8H), 1.4–1.2 (m,8H), 0.85 (t,3H,J=6.6 Hz).

Utility

The compounds of the present invention are inhibitors of the enzyme acyl-CoA: cholesterol acyltransferase and are thus effective in inhibiting esterification and transport of cholesterol across the intestinal wall. In addition, the compounds are useful in preventing the formation of cholesterol ester rich macrophages (foam cells) in the arterial wall through the inhibition of cholesterol ester formation. Foam cells are a source of the large quantity of cholesterol ester found in atheromatous lesions as opposed to the surrounding undiseased tissue. Thus inhibition of ACAT would decrease the accumulation and storage of cholesterol esters in the arterial wall and prevent or inhibit the formation of atheromatous lesions.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for eighteen hours prior to being sacrificed by decapitation. The livers were perfused in situ with 50 mL of cold 0.25 M sucrose, excised, and homogenized in three volumes of 0.1M phosphate buffer, pH 7.4, that contained 0.5 mM EDTA (ethylenediaminetetraacetic acid), 1.0 mM glutathione, 0.25 M sucrose and 20 µM leupeptin. Microsomes were obtained by differential centrifugation. The supernatant from an initial spin at 15,000 ×g for 15 minutes was centrifuged at 105,000 ×g for 1 hour to pellet the microsomes. The microsomes were suspended in 0.1M phosphate buffer with 1 mM GSH, pH 7.4, reisolated by centrifugation, and stored at −70° C.

The control assay in a final volume of 200 µL consisted of 200 µg of microsomal protein, 77 µM $^{14}$C-oleoyl-CoA (10,000 dpm/nmol) in 0.1M phosphate, pH 7.4, that contained 1 mM glutathione. Compounds were added in 5 µL of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min by the addition of 4 mL of chloroform:methanol (2:1::v:v). 30,000 dpm of $^{3}$H-cholesteryl oleate and 15 µg of unlabeled cholesteryl oleate and oleic acid were added as an internal standard and carriers, respectively. After allowing 20 min. for lipid extraction, 800 µL water was added to induce phase separation. The chloroform layer was transferred to another tube, dried under nitrogen and resuspended in 100 µL chloroform. Lipids were separated by thin layer chromatography using ITLC-SA thin layer plates (Gelman Sciences) and a solvent system of hexane:diethyl ether:acetic acid (170:30:1::v:v:v). The lipids were visualized by their interaction with iodine vapor and the cholesteryl ester spot was cut out and placed into a scintillation vial and counted. The specific activity of ACAT in the control incubation averaged 260 pmol/min/mg microsomal protein.

B. Assay of the Inhibition of Cholesterol Esterification in Mammalian Cells

The esterification of cholesterol was determined in the murine macrophage-like cell line J774.A1. Cells were seeded in 35 mm wells at a density of 300,000 cells per well in 2 mL of Dulbecco's Eagle Medium (DMEM) supplemented with 10% fetal bovine serum (FBS). Cells were incubated at 37° C. in an atmosphere of 5% $CO_2$ and 93% humidity. After 24 hours the media was changed to 0.68 mL 10% FBS-DMEM containing 34 µg of acetylated human low density lipoprotein (ac-LDL) to increase the intracellular concentration of cholesterol and promote esterification. At 41 hours, various inhibitors were added to the cells in DMSO (10 µL/mL maximum). At 43 hours, the cells were pulsed with 0.1 mM $^{14}$C-oleic acid (10,000 dpm/nmol) complexed with BSA (bovine serum albumin) to follow cholesterol ester formation. The experiment was terminated at 45 hours by washing the monolayers 3 times with 3 mL of Tris-buffered saline at 4° C. The lipids were extracted by incubating the monolayers with 1.5 ml of hexane: isopropanol (3:2::v:v) for 30 min. under gentle agitation. During this period, 10,000 dpm $^{3}$H-cholesteryl linoleate and 10 µg of cholesteryl oleate were added as an internal standard and carrier respectively. The organic solvent was removed and the cells were washed with an additional 1.0 mL of hexane: isopropanol which was combined with the original extract. The cells were allowed to dry overnight, digested with 1.5 mL of 0.2 N sodium hydroxide for 1 hour and an aliquot of the solubilized protein used for protein determination using the Lowry method. The organic extract was taken to dryness, resuspended in a solvent (3% diethyl ether, 97% hexane) for elution over a silica gel column and cholesterol esters extracted. Triglycerides were eluted with a solution of 25% diethyl ether in hexane. Scintillation cocktail was added to the eluted samples to determine the amount of radioactivity. The conversion of oleic acid to cholesteryl ester in the control averaged 0.54 mmol/hour/mg protein and was increased upon the addition of ac-LDL to about 10.69±0.69 mmol/hour/mg protein.

Using the assay methods described above, the compounds of this invention are found to exhibit an activity of at least $IC_{50}<50$ micromolar, thereby demonstrating and confirming the activity of these compounds as effective antihypercholesterolemic and/or antiatherosclerotic agents.

Dosage Forms

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences*, 16th Edition, 1980.

In their therapeutic use as antihypercholesterolemic and/or antiatherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient, nature and extent of symptoms, kind of concurrent treatment, frequency of treatment, and the effect desired. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

Syrup

|  | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension

|  | Wt. % |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

Resuspendable Powder

|  | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

|  | Wt. % |
|---|---|
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Semi-Solid Paste

|  | Wt. % |
|---|---|
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste

|  | Wt. % |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogeneous paste.

The term "consisting essentially of" in the present disclosure is intended to have its customary meaning, namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited publications and applications may provide further useful information, however, these cited materials are hereby incorporated by reference.

What is claimed is:

1. A compound of the formula (I):

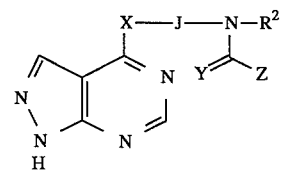

wherein:

X is $S(O)_r$, O, $NR^4$ or $CH_2$;

J is $C_2$–$C_{10}$ alkylene, $C_3$–$C_{10}$ alkenylene or $C_3$–$C_{10}$ alkynylene;

Y is O, S, or NH;

Z is $NHR^3$, $OR^3$ or $R^3$;

$R^1$ is selected independently from H, $NO_2$, Br, Cl, F, $CF_3$, CN, $CH_3S(O)_r$, $C_1$–$C_8$ alkyl or alkoxy, $C_1$–$C_4$ carboalkoxy, $NR_5R_6$ or $NR_5COR_6$;

$R^2$ is $C_1$–$C_8$ alkyl, $C_3$–$C_7$ cycloalkyl, $C_3$–$C_8$ alkenyl or alkynyl, $C_7$–$C_{14}$ araalkyl where the aryl group is optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; phenyl optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$ or $NR^5COR^6$; benzyl optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; 2-, 3-, or 4- pyridinyl, pyrimidinyl; or biphenyl;

$R^3$ is $C_3$–$C_7$ cycloalkyl, $C_4$–$C_{10}$ cycloalkylalkyl, $C_3$–$C_6$ alkenyl or alkynyl, $C_1$–$C_3$ perfluoroalkyl, $C_7$–$C_{14}$ araalkyl where the aryl group is optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; phenyl optionally substituted with 1 to 3 groups selected from $C_1$–$C_4$ alkyl or alkoxy, $C_3$–$C_8$ branched alkyl, F, Br, Cl, OH, CN, $CO_2H$, $CF_3$, $C_1$–$C_4$ carboalkoxy, $NR^5R^6$, or $NR^5COR^6$; benzyl optionally substituted with 1 to 3 groups selected from $C_1$–$C_4$ alkyl or alkoxy, F, Br, Cl, OH, CN, $CO_2H$, $CF_3$, $C_1$–$C_4$ carboalkoxy, $NR^5R^6$, or $NR^5COR^6$; 2-, 3-, or 4- pyridinyl, pyrimidinyl; or biphenyl;

$R^4$ is H, $C_1$–$C_6$ alkyl or benzyl;

$R^5$ and $R^6$ are selected independently from H or $C_1$–$C_4$ alkyl;

r is 0 to 2;

or a pharmaceutically acceptable salt thereof.

2. A compound of claim 1 wherein:

X is $S(O)_r$;

J is $C_2$–$C_{10}$ alkylene or $C_4$–$C_9$ branched alkylene;

Y is O;

Z is $NHR_3$;

$R^1$ is selected independently from H, $NO_2$, $C_1$–$C_8$ alkyl or alkoxy, $C_3$–$C_8$ branched alkyl, $C_1$–$C_4$ carboalkoxy, $NR^5R^6$ or $NR^5COR^6$;

$R^2$ is $C_1$–$C_8$ alkyl, $C_3$–$C_7$ cycloalkyl, $C_7$–$C_{14}$ araalkyl where the aryl group is optionally substituted with 1 to 3 groups selected from $CH_3$, $CH_3O$, F, Br, Cl, OH, CN, $CO_2H$, $CF_3$, $NH_2$, $NO_2$, or di($C_1$–$C_4$) alkylamino; phenyl optionally substituted with 1 to 3 groups selected from $CH_3$, $CH_3O$, F, Br, Cl, OH, CN, $CO_2H$, $CF_3$, $NH_2$, $NO_2$, or di($C_1$–$C_4$)alkylamino; benzyl optionally substituted with 1 to 3 groups selected from $CH_3$, $CH_3O$, F, Br, Cl, OH, CN, $CO_2H$, $CF_3$, $NH_2$, $NO_2$, or di($C_1$–$C_4$)alkylamino; 2-, 3-, or 4-pyridinyl, pyrimidinyl; or biphenyl;

$R^4$ is H.

3. A compound of claim 1 wherein:

X is S;

J is $C_2$–$C_{10}$ alkylene;

$R^1$ is selected from H, $CH_3$ or $NO_2$;

$R^2$ is $C_1$–$C_8$ alkyl, $C_7$–$C_{14}$ araalkyl where the aryl group is optionally substituted with 1 to 3 groups selected from $CH_3$, $CH_3O$, F, $NH_2$, $NO_2$, or di($C_1$–$C_4$) alkylamino; phenyl optionally substituted with 1 to 3 groups selected from $CH_3$, $CH_3O$, F, $NH_2$, $NO_2$, or di($C_1$–$C_4$) alkylamino; benzyl optionally substituted with 1 to 3 groups selected from $CH_3$, $CH_3O$, F, $NH_2$, $NO_2$, or di($C_1$–$C_4$) alkylamino; 2-, 3-, or 4- pyridinyl, pyrimidinyl; or biphenyl;

$R^3$ is $C_1$–$C_8$ alkyl, $C_7$–$C_{14}$ araalkyl where the aryl group is optionally substituted with 1 to 3 groups selected from $C_1$–$C_4$ alkyl or alkoxy, F, $NH_2$, $NO_2$, $C_1$–$C_4$ carboalkoxy, or di($C_1$–$C_4$)alkylamino; phenyl optionally substituted with 1 to 3 groups selected from $C_1$–$C_4$ alkyl or alkoxy, F, $NH_2$, $NO_2$, $C_1$–$C_4$ carboalkoxy, or di($C_1$–$C_4$)alkylamino; benzyl optionally substituted with 1 to 3 groups selected from $C_1$–$C_4$ alkyl or alkoxy, F, $NH_2$, $NO_2$, $C_1$–$C_4$ carboalkoxy, or di($C_1$–$C_4$) alkylamino; 2-, 3-, or 4- pyridinyl, pyrimidinyl; or biphenyl.

4. The compound which is N'-(2,4-Difluorophenyl)-N-heptyl-N-[ 5-(1H-pyrazolo(3,4-d)pyrimidin-4-ylthio)pentyl] urea.

5. A method of treating hypercholesterolemia or atherosclerosis in a mammal comprising administering to the mammal a therapeutically effective amount of a compound of claim 4.

6. A pharmaceutical composition comprising an effective ACAT inhibiting amount or antihypercholesterolemic amount or antiatherosclerotic amount of a compound of claim 1 and a pharmaceutically acceptable carrier.

7. A pharmaceutical composition comprising an effective ACAT inhibiting amount or antihypercholesterolemic amount or antiatherosclerotic amount of a compound of claim 2 and a pharmaceutically acceptable carrier.

8. A pharmaceutical composition comprising an effective ACAT inhibiting amount or antihypercholesterolemic amount or antiatherosclerotic amount of a compound of claim 3 and a pharmaceutically acceptable carrier.

9. A method of treating hypercholesterolemia or atherosclerosis in a mammal comprising administering to the mammal a therapeutically effective amount of a compound of claim 3.

10. A pharmaceutical composition comprising an effective ACAT inhibiting amount or antihypercholesterolemic amount or antiatherosclerotic amount of a compound of claim 4 and a pharmaceutically acceptable carrier.

11. A method of treating hypercholesterolemia or atherosclerosis in a mammal comprising administering to the mammal a therapeutically effective amount of a compound of claim 1.

12. A method of treating hypercholesterolemia or atherosclerosis in a mammal comprising administering to the mammal a therapeutically effective amount of a compound of claim 2.

* * * * *